(12) United States Patent
Shenk et al.

(10) Patent No.: US 11,008,551 B2
(45) Date of Patent: *May 18, 2021

(54) METHOD TO INCREASE THE INFECTIVITY OF VIRUS PARTICLES

(71) Applicant: The Trustees of Princeton University, Princeton, NJ (US)

(72) Inventors: Thomas Shenk, Princeton, NJ (US); Nicole Gudleski O'Regan, Hatboro, PA (US); Todd M. Greco, Langhorne, PA (US); Ileana M. Cristea, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/054,590

(22) Filed: Aug. 3, 2018

(65) Prior Publication Data

US 2018/0346885 A1 Dec. 6, 2018

Related U.S. Application Data

(63) Continuation of application No. 14/233,810, filed as application No. PCT/US2012/047534 on Jul. 20, 2012, now Pat. No. 10,174,290.

(60) Provisional application No. 61/510,298, filed on Jul. 21, 2011.

(51) Int. Cl.
| | | |
|---|---|---|
| *C12N 7/00* | (2006.01) | |
| *A61K 39/25* | (2006.01) | |
| *C12Q 1/70* | (2006.01) | |

(52) U.S. Cl.
CPC ............... *C12N 7/00* (2013.01); *C12Q 1/705* (2013.01); *A61K 39/25* (2013.01); *C12N 2710/16151* (2013.01)

(58) Field of Classification Search
None
See application file for complete search history.

(56) References Cited

U.S. PATENT DOCUMENTS

| 5,360,736 | A | 11/1994 | Provost et al. | |
|---|---|---|---|---|
| 7,169,559 | B2 | 1/2007 | Reid et al. | |
| 10,174,290 | B2 * | 1/2019 | Shenk | C12N 7/00 |
| 2008/0226594 | A1 | 9/2008 | Nauwynck et al. | |

OTHER PUBLICATIONS

Gudleski-O'Regan et al., Increased expression of LDL receptor-related protein 1 during human cytomegalovirus infection reduces virion cholesterol and infectivity, Cell Host Microbe, vol. 12, No. 1, pp. 86-96.*

Boucher et al., Signaling through LRP1: Protection from atherosclerosis and beyond, *Biochem. Pharmacol.*, 81:1-5 (2011).
Christian et al., Use of cyclodextrins for manipulating cellular cholesterol content, *J. Lipid Res*, 38(11):2264-72 (1997).
Gaultier et al., LDL Receptor-Related Protein 1 Regulates the Abundance of Diverse Cell-Signaling Proteins in the Plasma Membrane Proteome, *J. Proteome. Res.*, 9:6689-95 (2010).
Hodits et al., An antibody fragment from a phage display library competes for ligand binding to the low density lipoprotein receptor family and inhibits rhinovirus infection, J. Biol. Chem., 270(41):24078-85 (Oct. 1995).
International Preliminary Report on Patentability, PCT/US2012/047534, dated Jan. 21, 2014.
International Search Report and Written Opinion of the International Searching Authority, United States Patent Office, PCT/US2012/047534, dated Oct. 4, 2012.
Kawata et al., Role of LRP1 in transport of CCN2 protein in chondrocytes, J. Cell Sci., 125(Pt. 12):2965-72 (Jun. 2012).
Konecsni et al., Low pH-Triggered Beta-Propeller Switch of the Low-Density Lipoprotein Receptor Assists Rhinovirus Infection, J. Virol., 83:10922-30 (2009).
Lillis et al., LDL receptor-related protein 1: unique tissue-specific functions revealed by selective gene knockout studies, *Physiol Rev.*, 88(3):887-918 (2008).
Mercer et al., Vaccinia virus uses macropinocytosis and apoptotic mimicry to enter host cells, *Science*, 320(5875):531-5 (2008).
Munger et al., Dynamics of the cellular metabolome during human cytomegalovirus infection, *PLoS Pathog.*, 2:e132 (2006).
Munger et al., Systems-level metabolic flux profiling identifies fatty acid synthesis as a target for antiviral therapy, *Nat. Biotech.*, 26:1179-86 (2008).
Orr et al., Low density lipoprotein receptor-related protein is a calreticulin coreceptor that signals focal adhesion disassembly, *J. Cell Biol.*, 161(6):1179-89 (2003).
Prasad et al., Generation of a Potent Low Density Lipoprotein Receptor-related Protein 1 (LRP1) Antagonist by Engineering a Stable Form of the Receptor-associated Protein (RAP) D3 Domain, J. Biol. Chem., 290(28):17262-8 (Jul. 2015).
Quinn et al., Soluble low density lipoprotein receptor-related protein (LRP) circulates in human plasma, J. Biol. Chem., 272(38):23946-51 (Sep. 1997).
Terrand et al., LRP1 controls intracellular cholesterol storage and fatty acid synthesis through modulation of Wnt signaling, *J. Biol. Chem.*, 284(1):381-8 (2009).
Thorp et al., Requirements for CEACAMs and cholesterol during murine coronavirus cell entry, J. Virol., 78(6):2682-92 (Mar. 2004).
Vash et al., Three complement-type repeats of the low-density lipoprotein receptor-related protein define a common binding site for RAP, PAI-1, and lactoferrin, Blood, 92(9):3277-85 (Nov. 1998).
Viard et al., Role of Cholesterol in Human Immunodeficiency Virus Type 1 Envelope Protein-Mediates Fusion with Host Cells, *J. Virol.*, 76(22):11584-95 (2002).
Willnow et al., Low density lipoprotein receptor-related protein and gp330 bind similar ligands, including plasminogen activator-inhibitor complexes and lactoferrin, an inhibitor of chylomicron remnant clearance, J. Biol. Chem., 267(36):26172-80 (Dec. 1992).
Zhou et al., LRP1 controls cPLA2 phosphorylation, ABCA1 expression and cellular cholesterol export, *PLoS One*, 4(8):e6853 (2009).
Zhou et al., LRP1 regulates architecture of the vascular wall by controlling PDGFRbeta-dependent phosphatidylinositol 3-kinase activation, *PLoS One*, 4(9): e6922 (2009).

* cited by examiner

*Primary Examiner* — Benjamin P Blumel
(74) *Attorney, Agent, or Firm* — Marshall, Gerstein & Borun LLP

(57) ABSTRACT

A method for enhancing infectivity of HCMV virus particles is provided.

2 Claims, 6 Drawing Sheets

A

B

METHOD TO INCREASE THE INFECTIVITY OF VIRUS PARTICLES

CROSS-REFERENCED TO RELATED APPLICATION

This application is a Continuation of U.S. patent application Ser. No. 14/233,810, filed Apr. 7, 2014, which is a National Stacie Application of International Patent Application No. PCT/US2012/047534, filed Jul. 20, 2012, which claims the priority benefit of U.S. Provisional Patent Application No. 61/510,298, filed Jul. 21, 2011, the disclosure of which is incorporated herein by reference in its entirety.

This invention was made with government support under grant numbers CA082396 and DA026192 awarded by the National Institutes of Health. The government has certain rights in the invention.

BACKGROUND

Since the ability to obtain adequate yields of infectious virus can limit vaccine manufacturing, improved methods of virus production are always needed to meet an important industrial and medical need. Previous work (Munger et al., PLoS Pathog 2:e132, 2006; Munger et al., Nat Biotech 26:1179-86, 2008)) has demonstrated that human cytomegalovirus (HCMV) induces the synthesis of fatty acids, and, importantly, that the virus requires the de novo synthesis of fatty acids to generate an optimal yield of infectious progeny. Despite this understanding, U.S. Pat. No. 5,360,736 discloses that the addition of lipids during growth of certain viruses, and in particular after initiation of infection of the cultured cells, inhibits virus production.

Preparation of stock virus is necessary for development of therapeutic methods and materials. Accordingly, improved methods for virus production are useful for improving the yield of infectious virus, and more specifically for vaccine production.

DESCRIPTION OF THE INVENTION

A method for enhancing the infectivity of HCMV virus particles is described. The method of the disclosure is useful to increase infectivity of HCMV particles in a "live" virus preparation, and in particular, a vaccine, providing a manufacturing advantage over methods known in the art. In general, a method is provided for production of virus particles in a virus-infected host cell comprising the step of contacting the cell with a compound that induces the production of virus particles with increased infectivity, wherein the progeny virus particles produced in the cell in the presence of the compound display increased ability to successfully initiate infection of cells compared to virus particles produced in the cells in the absence of the compound. It will be readily apparent that each aspect of each embodiment of the method described herein is embraced and attaches to this general method. Production of virus is measured, in various aspects, by (i) the number of infectious virus particles, (ii) the number of virus particles, infectious and non-infectious, (iii) an amount of a specific viral antigen, and/or (iv) combinations of (i)-(iii).

In one embodiment, a method is provided for production of virus particles in a virus-infected host cell comprising the step of contacting the cell with a compound that decreases activity of low density lipoprotein related receptor 1 (LRP1), wherein the virus particles produced in the cell in the presence of the compound display increased infectivity compared to virus particles produced in the cell in the absence of the compound. In various aspects, the compound decreases LRP1 binding activity, the compound binds LRP1 and blocks LRP1 binding activity, the compound is a blocking antibody, and/or the compound is an extracellular fragment of LRP1. In various aspects, the compound decreases transcription and/or translation of a polynucleotide encoding LRP1, the compound decreases surface expression of LRP1, the compound decreases mobilization of LRP1 to a cell membrane, and/or the compound induces an inactive conformation of LRP1 at a cell membrane. LRP1 is also known as alpha-2-macroglobulin receptor (A2MR), apolipoprotein E receptor (APOER) or cluster of differentiation 91 (CD91). LRP1 has been shown to interact with, at least, apolipoprotein E, lipoprotein lipase, urokinase receptor, MAPK8IP2, tissue plasminogen activator, thrombospondin 1, SYNJ2BP, DLG4, NOS1AP, calreticulin, APBB1, ITGB1BP1, MAPK8IP1, GIPC1 and SHC1. Accordingly, LRP1 binding activity includes interaction with one or more of these proteins and any other LRP1 binding partner.

Also provided is a method for production of virus particles in a virus-infected host cell comprising the step of contacting the cell with a compound that increases intracellular cholesterol, wherein the virus particles produced in the cell in the presence of the compound display increased infectivity compared to virus particles produced in the cell in the absence of the compound. In various aspects, the compound increases cholesterol import into a cell, decreases cholesterol export from a cell, or both. In various aspects of the method, the compound modulates LDL-cholesterol receptor (LDLR) activity, the compound modulates ABCA1 activity, the compound is cholesterol, a cholesterol derivative or a cholesterol ester at an amount effective to increase intracellular levels of cholesterol. In various aspects, the compound decreases LRP1 activity, the compound decreases LRP1 binding activity, the compound binds LRP1 and blocks LRP1 binding activity, the compound is a blocking antibody, the compound is an extracellular fragment of LRP1, the compound decreases transcription and/or translation of a polynucleotide encoding LRP1, and/or the compound decreases surface expression of LRP1. In aspects utilizing cholesterol, a cholesterol derivative, or a cholesterol ester, the cholesterol, cholesterol derivative, or cholesterol ester is present at a concentration of at least 5 μM, at least 10 μM, at least 15 μM, at least 20 μM, at least 25 μM, at least 30 μM, at least 35 μM, at least 40 μM, at least 45 μM, at least 50 μM, at least 55 μM, at least 60 μM, at least 65 μM, at least 70 μM, at least 75 μM, at least 80 μM, at least 85 μM, at least 90 μM, at least 95 μM, at least 100 μM, at least 110 μM, at least 120 μM, at least 130 μM, at least 140 μM, at least 150 μM or more but at a concentration that is not toxic to the host cell. In various aspects, the method utilizes cholesterol that is present at a concentration of no more than 5 μM, no more than 10 μM, no more than 15 μM, no more than 20 μM, no more than 25 μM, no more than 30 μM, no more than 35 μM, no more than 40 μM, no more than 45 μM, no more than 50 μM, no more than 55 μM, no more than 60 μM, no more than 65 μM, no more than 70 μM, no more than 75 μM, no more than 80 μM, no more than 85 μM, no more than 90 μM, no more than 95 μM, no more than 100 μM, no more than 110 μM, no more than 120 μM, no more than 130 μM, no more than 140 μM, or no more than 150 μM.

In various aspects of each embodiment of the method provided, the cell is contacted with the compound prior to virus infection, the cell is contacted with the compound after virus infection or the cell is contacted with the compound concurrently with virus infection.

In various aspects of each embodiment of the method, the virus is an enveloped virus, the virus is an enveloped DNA virus or an enveloped RNA virus, the virus is a herpes virus, the virus is an alpha family herpes virus, the virus is a beta family herpes virus, the virus is an gamma family herpes virus, the virus is CMV, and/or the virus is a pox virus, a non-envelope picorna virus, an RNA virus influenza virus, herpes simplex virus, Epstein Barr virus, hepatitis C virus, Dengue virus, HIV, mumps virus, measles virus, and/or parainfluenza virus.

In various aspects of each embodiment of the method, the cell is a eukaryotic cell, the cell is a mammalian cell or the cell is a human cell.

In each embodiment of the method provided, in various aspects, the method optionally further comprises the step of isolating the virus from medium of cell growth. In various aspects, the method further comprises the step of isolating the virus from the host cell.

In each embodiment of the method provided, in various aspects, the method optionally, comprises the step of infecting the host cells with the virus. In various aspects, the host cell is infected at a multiplicity of infection (MOI), including e.g. and without limitation, 0.0001, 0.001, 0.01, 0.1, 1.0, 3, 5, 10 or more infectious units per cell.

In each embodiment of the method provided, in various aspects, the method optionally further comprises the step of growing the host cells to confluence, to about 90%, about 80% confluence, about 70% confluence, about 60% confluence, about 50% confluence, or less than 50% confluence prior to infecting the host cells with the virus.

In each embodiment of the method provided, in various aspects, the method optionally further comprises the step of culturing the host cells after infecting the host cells with the virus.

In each embodiment of the method provided, in various aspects, the method optionally further comprises the step of adding or changing medium of growth for the host cells prior to isolating the virus.

In each embodiment of the method provided, in various aspects, the method optionally further comprises the step of incubating the host cells with an infecting virus for an adsorption period.

EXAMPLES

The invention is further described in the following examples. The examples serve only to illustrate the invention and are not intended to limit the scope of the invention in any way.

Example 1

The majority of disease biomarkers and drug targets are membrane proteins, and previous studies have demonstrated changes occur at the surface of virus-infected cells.

Figure 1:
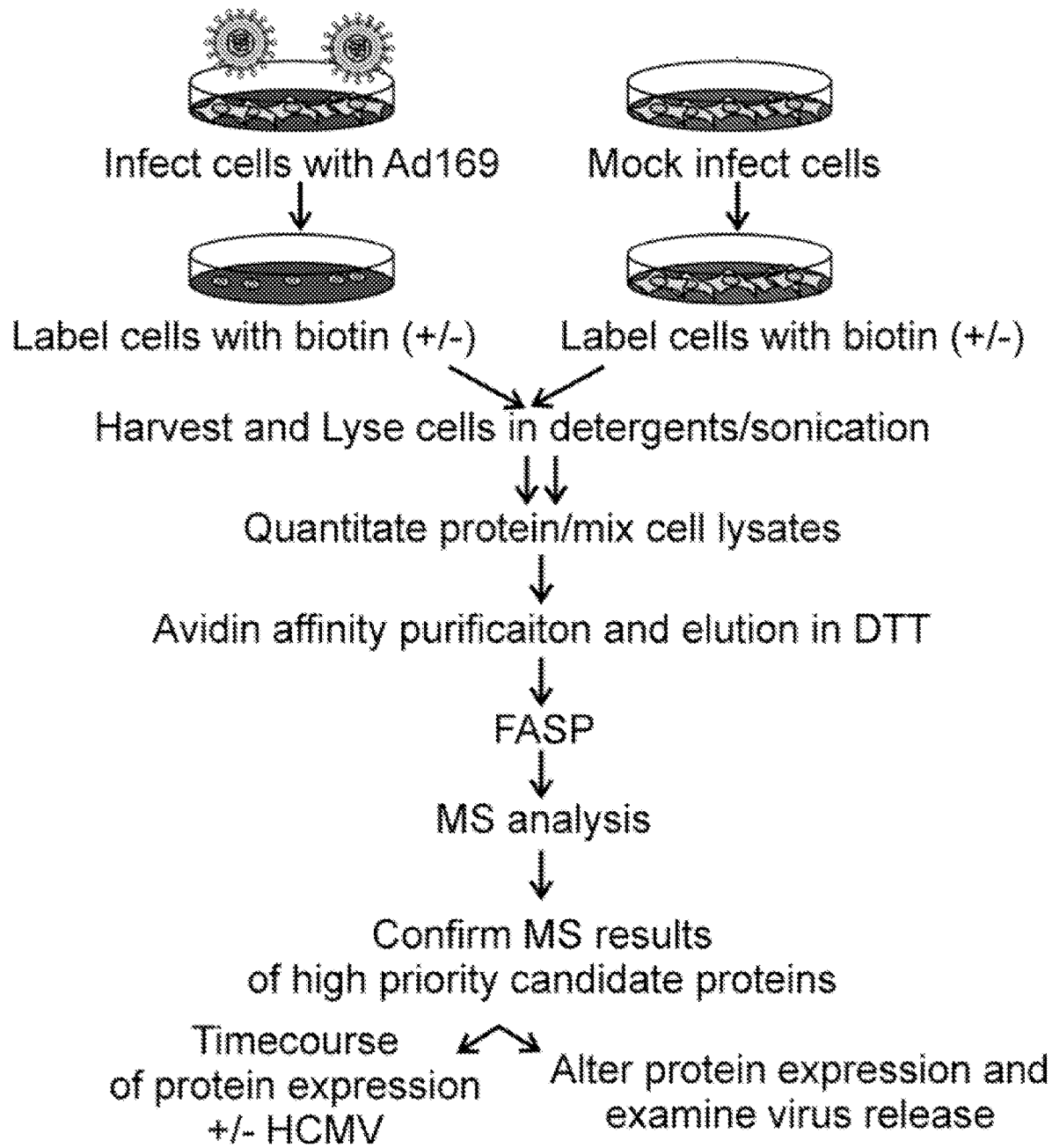
FIG. 1. Strategy to identify PM protein alterations in HCMV-infected cells.

Consequently, an experiment was performed to identify changes in cellular plasma membrane (PM) protein expression following virus infection. The PM proteome of uninfected fibroblasts was compared to that of HCMV-infected fibroblasts using mass spectrometry (MS) analysis of affinity purified PM proteins. The experimental design is outlined in FIG. 1.

In short, MRC5 fibroblasts were mock infected or infected with HCMV strain AD169 at a multiplicity of 5 pfu/cell. After 6, 24, or 72 hours, cell surface proteins were biotinylated, lysed in detergents and sonicated. Biotinylated proteins were bound to an avidin matrix, and samples were eluted with DTT. Filter-aided sample preparation (FASP) was used to concentrate the sample, remove detergents, and unfold the proteins. Isolated proteins were digested with trypsin, and peptides were analyzed by mass spectrometry (MS).

Results from mass spectrometry analysis identified multiple PM proteins whose levels changed after infection. One of proteins was the low density lipoprotein related receptor 1 LRP1, for recent reviews of LRP1 function see (Lillis, Van Duyn et al. 2008; Boucher and Herz 2010; Gaultier, Simon et al. 2010).

Example 2

Western blot analysis was then carried out to confirm these initial results. Fibroblasts were mock infected or infected at a multiplicity of 5 pfu/cell with HCMV strain AD169, and the level of LRP1 in whole cell extracts (WCL) and plasma membrane (PM) were determined by western blot at 6, 12, 24, 48 and 72 hours later. β-actin and insulin receptor (IR) levels were assayed as controls.

Figure 2:
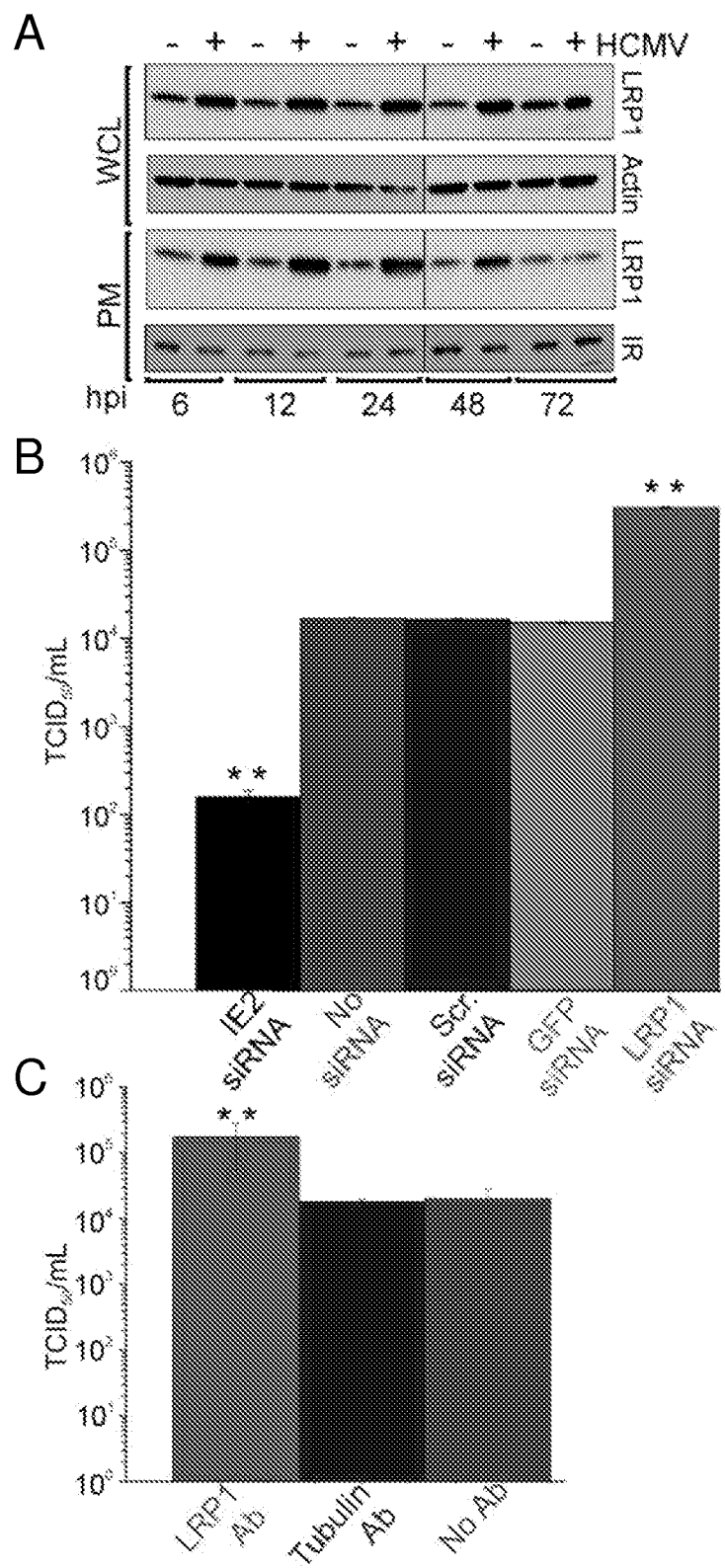
FIG. 2. LRP1 levels are induced after infection, and LRP1 modulates the production of HCMV progeny.

Results from the western blot analysis confirmed that total cellular and PM-associated LRP1 was elevated at 6, 24 and 48 hours after infection (FIG. 2A).

Since protein level changed, the possibility that LRP1 performs an important function during HCMV infection was tested using siRNA knockdown to reduce protein level or a blocking/neutralizing antibody to decrease protein activity.

At 24 hours after siRNA transfection or 1 hour after antibody treatment, fibroblasts were infected at a multiplicity of 0.1 PFU/cell with HCMV strain AD169. 96 hours later, virus in culture medium was quantified by $TCID_{50}$ assay. IE2-specific siRNA served as a positive control; scrambled (Scr) and GFP-specific siRNAs served as negative controls; tubulin-specific antibody served as a negative control. **$P<0.001$ (t-test, compared to scrambled siRNA or tubulin antibody).

Knockdown of LRP1 protein levels with siRNA increased the production of HCMV by more than a factor of 10 (FIG. 2B), and a similar increase was observed when LRP1 antibody (Orr, Pedraza et al. 2003) was used to neutralize LRP1 activity (FIG. 2C). Error bars represent the standard errors of the means from three independent experiments, each performed in triplicate. These experiments demonstrate that LRP1 restricts or inhibits the production of HCMV infectivity, and infectivity can be increased if the level of LRP1 protein or its activity is reduced.

Example 3

In order to determine whether the observed change in infectivity of the virus results from a change in actual virus particle number, the following experiment was carried out.

LRP1-specific siRNA-treated fibroblasts were infected with HCMV strain AD169 at a multiplicity of 5 PFU/cell. Cells were harvested at the indicated times, and the accumulation of IE1 (HCMV immediate-early protein), pUL44 (HCMV early protein), pUL99 (HCMV late protein), β-actin (loading control), and LRP1 were analyzed by Western blot. hpi=hours post infection.

Figure 3:
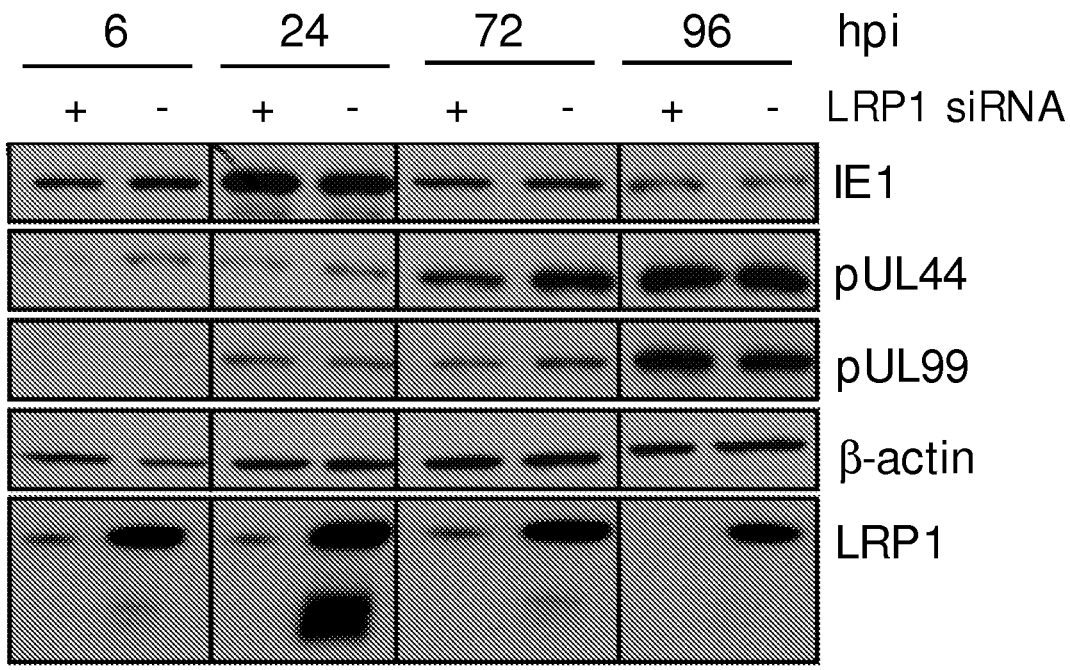
FIG. 3. LRP1 knockdown has little effect on the accumulation viral proteins and DNA, but causes a dramatic increase in virion infectivity.
Figure 3:
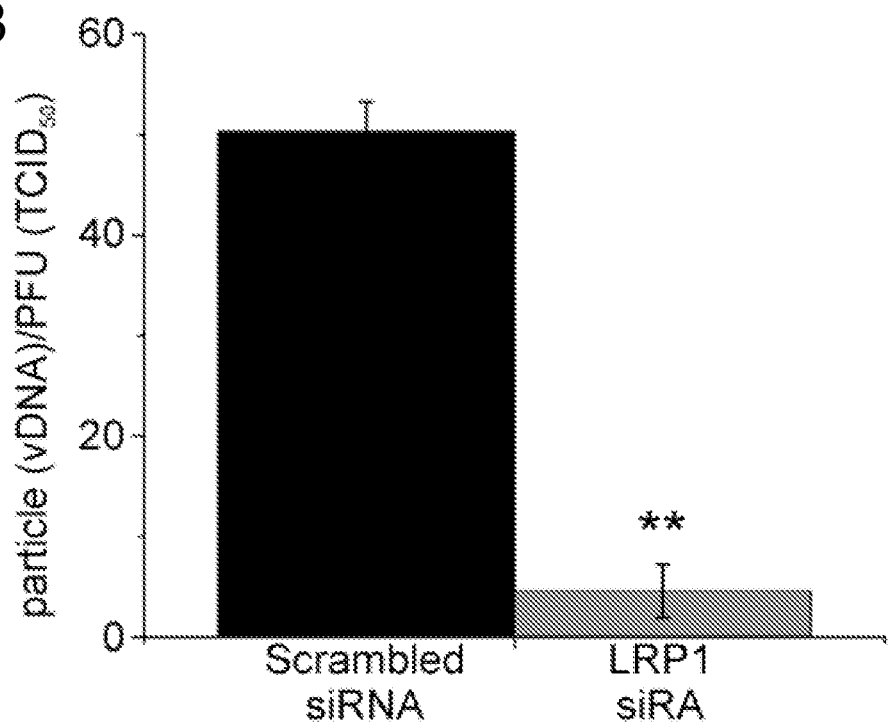

Under conditions where the production of HCMV infectivity was enhanced by siRNA-mediated knockdown of LRP1, little difference was observed in the accumulation of a representative immediate-early (IE1), early (pUL44) or late (pUL99) viral protein (FIG. 3A).

Particle to PFU ratios were calculated for partially purified virions by dividing the amount of DNA in virus particles (quantified by qPCR with UL123-specific primers) by the virus titer (quantified by $TCID_{50}$). Error bars represent the standard errors of the means from two independent experiments, each performed in triplicate. **$P<0.001$ (t-test).

The particle/PFU ratio decreased by a factor of about 10 (FIG. 3B), demonstrating that viral particles are more infectious when made in cells with reduced LRP1 activity.

Example 4

LRP1 has been shown to prevent intracellular accumulation of free cholesterol and cholesterol esters by stimulating a Wnt5a signaling pathway (Terrand, Bruban et al. 2009). In order to determine whether the change in LRP1 activity seen with virus infection alters cellular cholesterol, the following experiment was carried out.

MRC5 fibroblasts were left untreated, transfected with siRNAs (LRP1 or scrambled control), or treated with antibodies (LRP1 or tubulin), then left uninfected or infected with HCMV strain AD169 at a multiplicity of 0.1 or 5 pfu/cell. At 24 (A) or 96 (B) hpi, the cholesterol content of MRC5 cells was quantified using the amplex red (Invitrogen) specrofluorometric assay. Total cholesterol corresponds to free+esterified cholesterol per 100,000 MRC5 cells.

Figure 4:
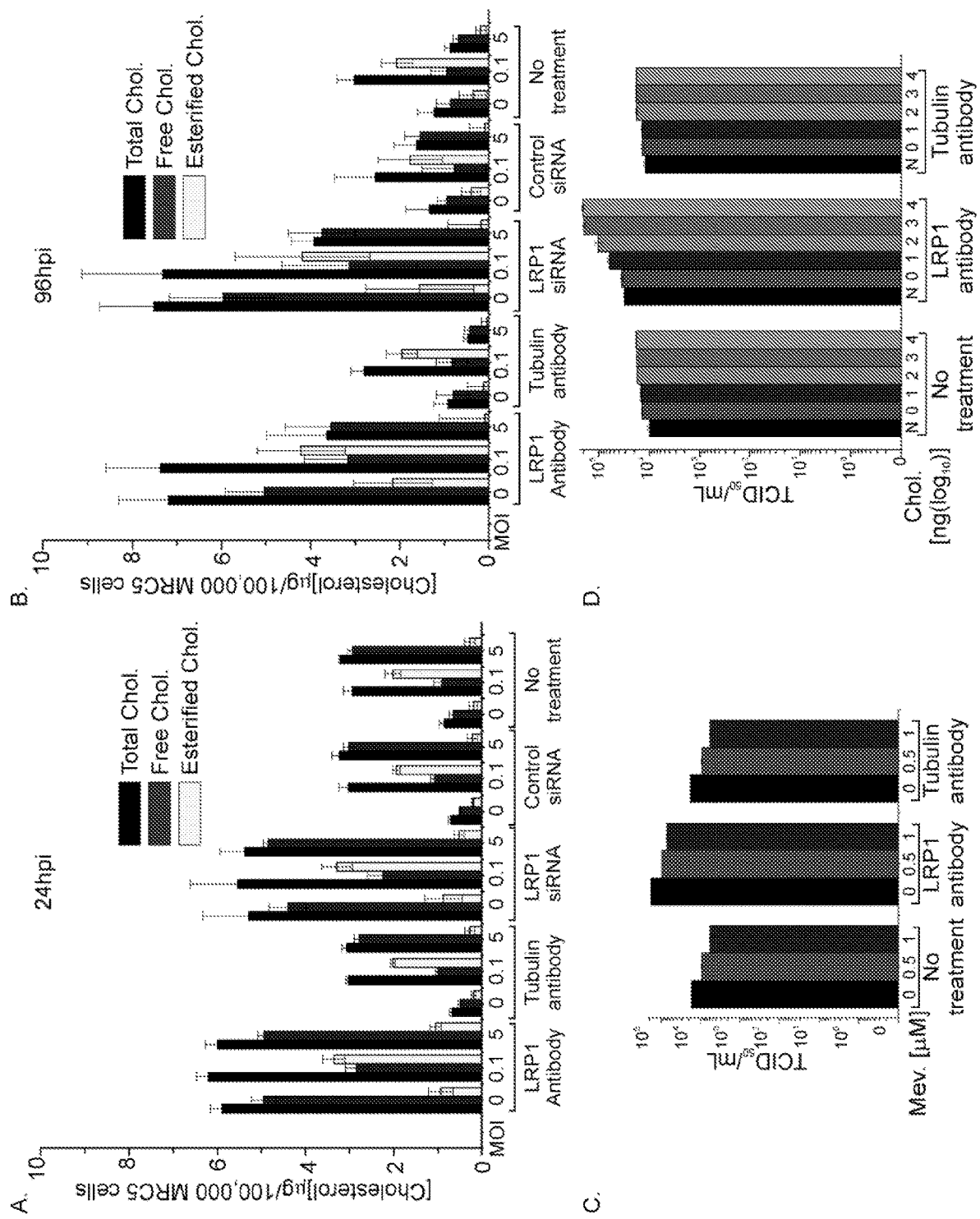
FIG. 4. Cholesterol content is increased in LRP1 knockdown cells via increased cholesterol import, not de novo synthesis.

Results demonstrated that cellular cholesterol levels were increased by treatment of infected cells with LRP1-specific siRNA or LRP1 antibody (FIGS. 4A and B).

In order to assess the mechanism by which cellular cholesterol changes, the following experiments were carried out.

In a first experiment, MRC5 cells were left untreated, treated with Mevastatin or mock treated. At 90 minutes post Mevastatin treatment, cells were treated with antibody to LRP1 or tubulin or left untreated. 1 hour post Mevastatin treatment, cells were infected at a multiplicity of 0.1 PFU/cell. At 96 hpi, released virus was used to infect new cells.

In a second experiment, cells were serum starved for 48 hours then treated with indicated antibodies. 1 hour post antibody treatment, serum-starved, confluent MRC5 cells were treated with various concentrations of cholesterol (+fatty acid-free BSA carrier) for 1 hour then infected at a multiplicity of 0.1 PFU/cell. At 96 hpi, released virus was used to infect new cells. "N" indicates no added cholesterol. Cell-free virus was quantified by a $TCID_{50}$ assay. Data represents the mean and standard deviation from three independent experiments with three replicates each.

Results showed that intracellular cholesterol levels influenced the production of HCMV infectivity in two ways. First, cells were treated with Mevastatin to inhibit HMG-CoA reductase and thereby block de novo cholesterol biosynthesis within infected cells; and, although the effect was modest, the drug inhibited the production of infectivity in a dose-dependent manner (FIG. 4C). Second, cultures were supplemented with cholesterol and the supplementation substantially enhanced the production of HCMV infectivity by cells that were also treated with LRP1-specific antibody (FIG. 4D). Mevastatin reversed the increased infectivity caused by inhibition of LRP1 activity to a limited extent and cholesterol supplementation demonstrated that LRP1 had little effect in the absence of extracellular cholesterol. Thus, cholesterol import is at least partly responsible for increased infectivity produced when LRP1 function is antagonized.

Example 5

Previous studies have shown that ABCA1 (a cellular cholesterol export receptor) expression is positively regulated by LRP1 (Zhou, Choi et al. 2009) and the low density lipoprotein receptor (LDLR) PM localization is negatively regulated by LRP1 (Zhou, Takayama et al. 2009). Accordingly, experiments were designed to test whether the increased cholesterol import and overall increase in intracellular cholesterol content in LRP1 knockdown cells was due to altered expression of these proteins.

Protein levels of LDLR were upregulated and ABCA1 were downregulated upon LRP1 knockdown (data not shown). Virus infection alone has the same effect as LRP1 knockdown, but to a lesser degree (data not shown). Further, it was observed that siRNA knockdown of LDLR partially reversed the increase in infectivity and intracellular cholesterol content resulting from LRP1 knockdown. Together, these results suggest that altered expression of LDLR and ABCA1 caused by LRP1 knockdown result in an overall increase in intracellular cholesterol levels with an increase in virion infectivity.

Example 6

Due to the ability to sequester cholesterol in its hydrophobic pocket, methyl-ß-cyclodextrin (MCβD) removes cholesterol from membranes (Christian, Haynes et al. 1997). Thus, in order to directly test the role of virion envelope cholesterol in HCMV infection, purified virions were treated with various concentrations of MCβD to deplete cholesterol.

Figure 5:
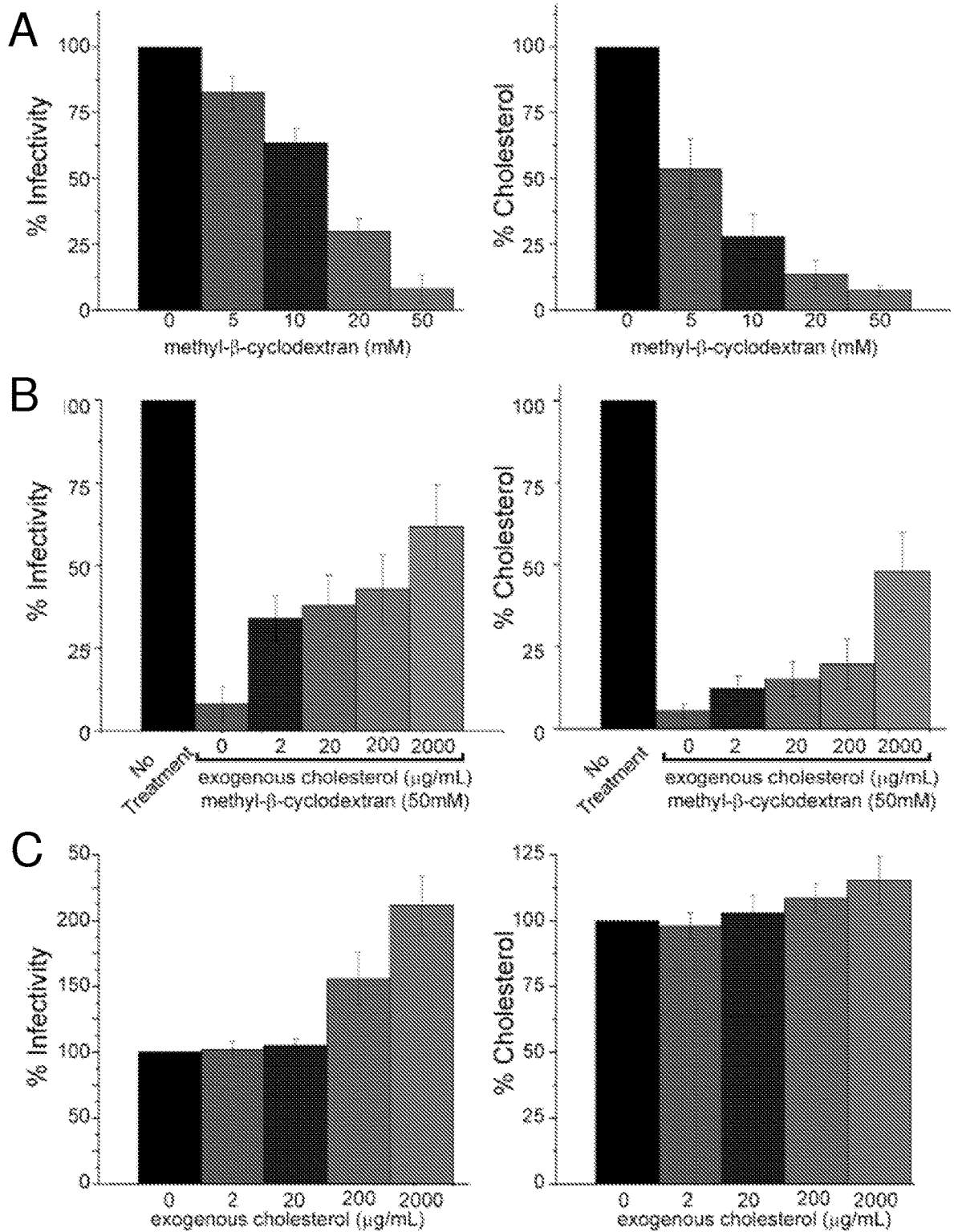
FIG. 5. Cholesterol content in virus particles regulates virus infectivity.

Gradient purified HCMV strain AD169 virions were either mock treated or treated with increasing concentrations of MCβD for 30 min at 37° C. MCβD (50 mM) treated virus was incubated in varying concentrations of cholesterol for 30 min at 37° C. Virus (no MCβD treatment) was incubated in varying concentrations of cholesterol for 30 min at 37° C. In all experiments, infectivity (FIG. 5, left panels) and cholesterol content (FIG. 5, right panels) were determined for the treated samples. Infectivity of untreated virus was set to 100%. Virus cholesterol content was determined using the amplexred (Invitrogen) specrofluorometric assay.

Results showed that incubation of virus particles with MCβD resulted in a dose-dependent inhibition of HCMV infectivity (FIG. 5A, left).

To confirm that MCβD treatment depleted virus of envelope cholesterol, the cholesterol content of MCβD-depleted virus was determined (FIG. 5A, right). Treatment achieved a dose-dependent decrease in cholesterol content, with 90% depletion obtained with 50 mM MCβD, thus confirming that MCβD treatment produces efficient depletion of virion envelope cholesterol which results in decreased virus infectivity.

To determine whether the effect of MCβD could be rescued (and is thus reversible), and moreover, to determine if the loss of infectivity was due to cholesterol depletion, exogenous cholesterol was used to replenish the envelopes of MCβD-treated virions by incubating the virus particles with various amounts of free cholesterol.

Results showed that incubation with cholesterol partially restored HCMV infectivity (FIG. 5B, left) and envelope cholesterol (FIG. 5B, right) content in a dose-dependent manner.

To determine if virus infectivity could be increased by increasing virion cholesterol content alone, gradient purified HCMV virions were incubated with increasing concentrations of cholesterol then gradient purified for a second time.

Results show that incubation with cholesterol increased virus infectivity (FIG. 5C, left) and overall cholesterol content (FIG. 5C, right) in a dose dependent manner, demonstrating that enhanced virion cholesterol content increases the infectivity of virions.

Example 7

It is known that infection of host cells by enveloped viruses relies on the fusion of the viral envelope with either an endosomal membrane or the plasma membrane of the cell. Therefore, experiments were designed to test whether infectivity of MCβD-treated virus can be restored by using an "acid bypass assay" (Mercer and Helenius 2008) to circumvent the normal membrane fusion process during virus entry.

Cells were infected with MCβD (50 mM)-treated or mock-treated HCMV strain AD169 at a multiplicity of 3 pfu/cell, allowed to sit at 4° C. for 30 min to allow virus binding, then treated with buffer at a neutral (7.4) or acidic (4.7) pH for 3 min, washed with PBS, and examined for IE1 expression 24 hours later.

Figure 6:
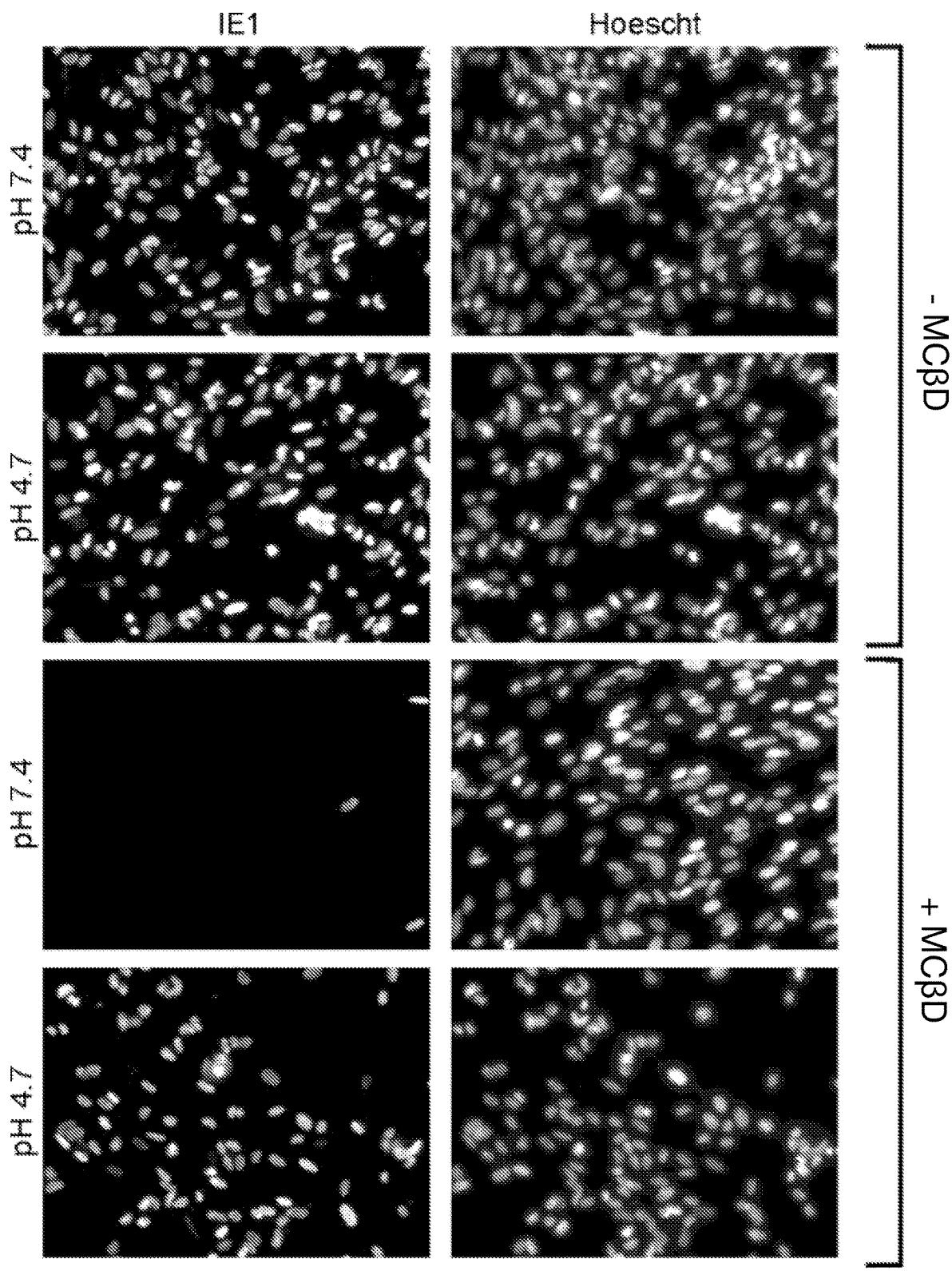
FIG. 6. Infectivity of cholesterol-depleted virus can be restored by circumventing the fusion step.

HCMV particles, either treated with MCβD or left untreated, were bound to cells at 4° C., then incubated in a low pH buffer (pH 4.7) to artificially induce the fusion event, thus allowing fusion-deficient viruses to enter the cell and replicate. A neutral pH buffer was used as a control. Virus replication after acid bypass was visualized by IE1 expression at 24 hpi (FIG. 6).

Results showed that acid bypass of the fusion event caused a dramatic difference in the ability of MCβD-treated viruses to enter the cell and express IE1 protein. These data demonstrate that the level of envelope cholesterol is important for HCMV fusion with host cells.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

Boucher, P. and J. Herz (2011). "Signaling through LRP1: Protection from atherosclerosis and beyond." *Biochem. Pharmacol.*, in press.

Christian, A. E., M. P. Haynes, et al. (1997). "Use of cyclodextrins for manipulating cellular cholesterol content." *J Lipid Res* 38(11): 2264-2272.

Gaultier, A., G. Simon, et al. (2010). "LDL Receptor-Related Protein 1 Regulates the Abundance of Diverse Cell-Signaling Proteins in the Plasma Membrane Proteome." *J. Proteome. Res.*

Lillis, A. P., L. B. Van Duyn, et al. (2008). "LDL receptor-related protein 1: unique tissue-specific functions revealed by selective gene knockout studies." *Physiol Rev.* 88(3): 887-918.

Mercer, J. and A. Helenius (2008). "Vaccinia virus uses macropinocytosis and apoptotic mimicry to enter host cells." *Science.* 320(5875): 531-535.

Orr, A. W., C. E. Pedraza, et al. (2003). "Low density lipoprotein receptor-related protein is a calreticulin coreceptor that signals focal adhesion disassembly." *J Cell Biol* 161(6): 1179-1189.

Terrand, J., V. Bruban, et al. (2009). "LRP1 controls intracellular cholesterol storage and fatty acid synthesis through modulation of Wnt signaling." *J. Biol. Chem.* 284(1): 381-388.

Zhou, L., H. Y. Choi, et al. (2009). "LRP1 controls cPLA2 phosphorylation, ABCA1 expression and cellular cholesterol export." *PLoS One* 4(8): e6853.

Zhou, L., Y. Takayama, et al. (2009). "LRP1 regulates architecture of the vascular wall by controlling PDGFR-beta-dependent phosphatidylinositol 3-kinase activation." *PLoS. One.* 4(9): e6922.

What is claimed is:

1. An in vitro method for production of virus particles in a virus-infected host cell comprising the step of contacting the cell with siRNA that decreases activity of LRP1, wherein the virus particles produced in the cell in the presence of the siRNA display increased infectivity compared to virus particles produced in the cell in the absence of the siRNA, and wherein the siRNA decreases the level of LRP1 protein.

2. An in vitro method for production of virus particles in a virus-infected host cell comprising the step of contacting the cell with siRNA that increases intracellular cholesterol, wherein the virus particles produced in the cell in the presence of the siRNA display increased infectivity compared to virus particles produced in the cell in the absence of the siRNA, and wherein the siRNA decreases the level of LRP1 protein.

* * * * *